United States Patent [19]

Yang

[11] Patent Number: 4,759,608

[45] Date of Patent: Jul. 26, 1988

[54] AUTOMATIC LIQUID CRYSTAL LIGHT-SHUTTER

[76] Inventor: Jong P. Yang, 4F, No. 124, Min Der St., Kaohsiung, Taiwan, 800

[21] Appl. No.: 815,016

[22] Filed: Dec. 31, 1985

[51] Int. Cl.⁴ .............................................. G02F 1/13
[52] U.S. Cl. ................................. 350/331 R; 350/332
[58] Field of Search ........................... 350/331 R, 332; 219/147

[56] References Cited

U.S. PATENT DOCUMENTS

| | | | |
|---|---|---|---|
| Re. 29,684 | 6/1978 | Gordon | 350/331 R |
| 4,039,803 | 8/1977 | Harsch | 350/331 R |
| 4,152,846 | 5/1979 | Witt | 350/331 R |
| 4,155,122 | 5/1979 | Budmiger | 350/331 R |
| 4,240,709 | 12/1980 | Hörnell | 350/331 R |
| 4,241,286 | 12/1980 | Gordon | 350/331 R |

FOREIGN PATENT DOCUMENTS

| | | | |
|---|---|---|---|
| 2315308 | 10/1973 | Fed. Rep. of Germany | 219/147 |
| 3349794 | 10/1974 | Fed. Rep. of Germany | 219/147 |

*Primary Examiner*—Stanley D. Miller
*Assistant Examiner*—Trong Q. Phan
*Attorney, Agent, or Firm*—Holman & Stern

[57] ABSTRACT

An automatic liquid crystal light-shutter which detects directly the flashing light generated by an alternating current electric welding machine, by means of a photo diode detector and then converts the detected light into an alternating signal current. Then this signal current is filtered to remove miscellaneous signals, amplified and rectified. Next, the rectified signal is fed to an inverter circuit which controls the oscillating of an oscillating circuit that operates a liquid crystal display to function very swiftly.

2 Claims, 2 Drawing Sheets

1

AUTOMATIC LIQUID CRYSTAL LIGHT-SHUTTER

BACKGROUND OF THE INVENTION

As we know, strong lights are harmful to our eyes. But, in some jobs, strong lights, such as caused in electric welding, are unavoidable so that eye protection is quite indispensable.

In the earlier days, the way to protect the eyes was to wear blackcolored glasses which were inconvenient for wearers. Nowadays, though, there has been a sort of automatic liquid crystal light-shutter; it uses two photo diodes to detect respectively the direct light and the lateral light, changing them into electric signals which are compared in an electric circuit, enabling a liquid crystal display (LCD) controlled by the electric circuit to let light penetrate through or to shut it out according to the light difference.

The above-mentioned equipment based on comparing the different intensities of two lights is widely applied in a variety of devices. But it acts too slowly; when applied in detecting the light of electric welding so that strong light at the very beginning of work still more or less makes workers' eyes feel uncomfortable. Also, when a worker is working directly under the sunshine, the lateral light is so strong that it will influence the responding sensitivity, and when the object is reflective, the light reflected from the object will be erroneously detected as direct light, interrupting its detecting preciseness.

In order to improve the disadvantage of the above-mentioned equipment, the inventor has worked hard to provide this invention that is based on using a photo diode to detect directly the rapid flashing light caused by the AC power in electric welding and then makes use of an electric circuit for controlling a liquid crystal display to operate; quickly.

DETAILED DESCRIPTION OF THE INVENTION

Figure 1:
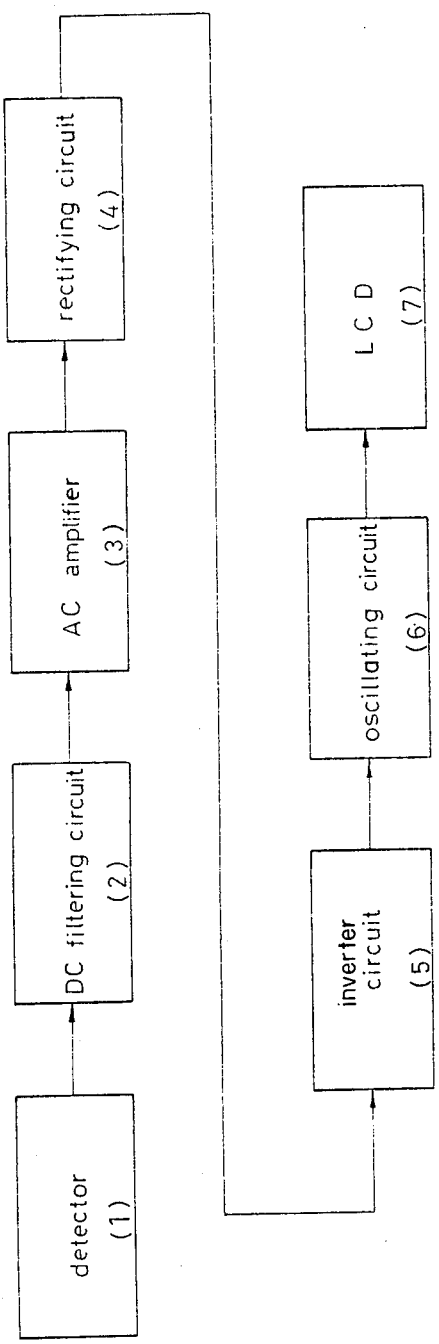
FIG. 1 is a functional diagram of the electric circuits in this invention.

As shown in FIG. 1, which is a functional block diagram of the electric circuits in this invention, the circuits include a detector 1, a DC filtering circuit 2, an AC amplifier 3, a rectifying circuit 4, an inverter circuit 5, an oscillating circuit 6 and a liquid crystal display (LCD).

Figure 2:
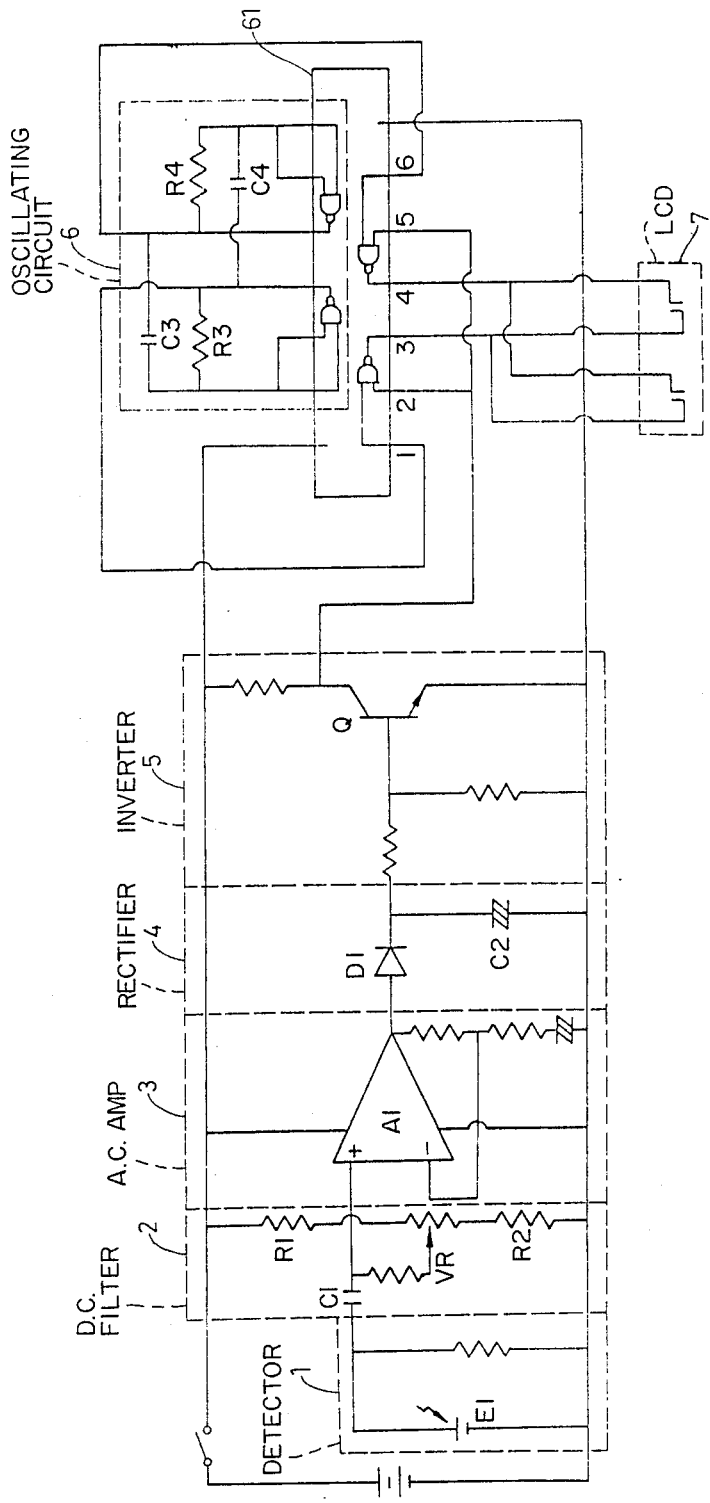
FIG. 2 is a detailed diagram of the electric circuits in this invention.

Next, FIG. 2 illustrates the detailed electric circuits of this invention. The detector 1 is composed of a photo diode E1; the DC filtering circuit 2 is an RC high-pass network composed of a condenser C1 and resistors R1, VR, R2; the AC amplifier 3 is an operational amplifier A1; the rectifying circuit 4 consists of a diode D1 and condenser C2; the inverter circuit 5 consists of a transistor Q; the oscillating circuit 6 is an RC oscillator composed of a NAND gate IC 61, resistors R3, R4 and condensers C3, C4; the liquid crystal display (LCD) 7 is made of liquid crystal.

The operation of the above-mentioned electric circuits is described in detail as follows.

When the light shutter is operating, through the detection action of the photo diode E1, the light energy detected is converted into an electric signal which is fed to the DC filtering circuit. Since the electric welding machine is commonly supplied with AC power, so the light derived from discharging will flash at the same frequency as that of the AC source. Also, the output of the photo diode E1 is an AC signal which is fed to the DC filtering circuit 2 that can filter out the DC signal and miscellaneous signals of low frequency, for this circuit 2 is a highpass network that allows only the exact AC current component derived in accordance with the detected welding light to pass. In addition, the DC filtering circuit 2 includes a variable resistor VR that is able to adjust the DC potential so as to adjust its sensitivity.

The AC signal, the output from the DC filtering circuit 2, is then fed to the AC amplifier 2 for amplification and next, fed to the rectifying circuit 4 that rectifies it into a DC voltage of high potential by means of the operation of a diode D1 and a condenser C2. This DC voltage serves to bias the base of the transistor Q in the inverter circuit 5 so that the transistor Q can become turned on and function. When the transistor Q is on, the output voltage of its collecter is low, and so are the voltages at pins 2, 5 of the NAND gate IC 61 in the oscillating circuit 6. Suppose that the input at pin 1 is high and that at pin 6 low, then pins 3, 4 give out an output of the same high voltage without potential difference. Therefore, the liquid crystal display 7 stays static in its black (dark) condition, attaining the purpose of shutting out the light.

On the contrary, when the photo diode E1 doesn't detect any welding light, the transistor Q becomes turned off and the output voltage of its collecter goes high, as are the inputs at pins 2, 5 at NAND gate IC 61. Suppose that the input of the pin 1 is high and that at pin 6 low, therefore, the output at pin 3 goes low and that at pin 4 high, forming a potential difference and enabling the liquid crystal display 7 to operate and become transparent so that it can be seen through clearly.

I claim:

1. An automatic liquid crystal light-shutter, comprising:
    detector means for detecting light and providing an electrical output signal in accordance with said detected light;
    filter means operably connected with said detector means for blocking signals below a predetermined frequency while passing signals above said predetermined frequency, said predetermined frequency corresponding to the frequency of an alternating welding current supplied by an alternating current electric welding machine and also corresponding to the frequency of the welding spark discharge of said alternating current electrical welding machine;
    amplifier means operably connected with said filter means for amplifying filtered signals output by said filter means;
    rectifier means operably connected with said amplifier means for rectifying amplified signals output from said amplifier means;
    inverter circuit means operably connected with said rectifier means for inverting rectified signals output by said rectifier means;
    oscillating circuit means operably connected with said inverter circuit means, for providing an oscillating output signal in accordance with one state of a signal input thereto from said inverter circuit means; and a liquid crystal display means operably connected with an output of said oscillating circuit means and operable for respectively blocking or transmitting light in accordance with the presence or absence of an oscillating output signal from said oscillating circuit means.

2. An automatic liquid crystal light-shutter according to claim 1, wherein said detector means includes a photo-diode, said filter means includes means for adjusting its sensitivity, and said oscillating circuit means includes a plurality of NAND gates.

* * * * *